United States Patent
Fujimoto et al.

(10) Patent No.: US 7,854,719 B2
(45) Date of Patent: Dec. 21, 2010

(54) METHOD OF INTRODUCING ULTRASONIC DRUG AND APPARATUS THEREOF

(75) Inventors: Katsuhiko Fujimoto, Saitama (JP); Keisuke Hashimoto, Nasushiobara (JP); Shigeharu Ohyu, Yaita (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 100 days.

(21) Appl. No.: 11/617,420

(22) Filed: Dec. 28, 2006

(65) Prior Publication Data
US 2007/0161944 A1 Jul. 12, 2007

(30) Foreign Application Priority Data
Jan. 6, 2006 (JP) .............................. 2006-001822

(51) Int. Cl.
A61B 17/20 (2006.01)
(52) U.S. Cl. ............................. 604/22; 604/19; 600/439
(58) Field of Classification Search ............. 604/19, 604/20, 22; 600/437, 439, 443; 601/2
See application file for complete search history.

(56) References Cited

U.S. PATENT DOCUMENTS

| | | | |
|---|---|---|---|
| 5,078,144 A | 1/1992 | Sekino et al. | |
| 5,267,985 A | 12/1993 | Shimada et al. | |
| 5,307,816 A | 5/1994 | Hashimoto et al. | |
| 5,445,611 A | 8/1995 | Eppstein et al. | |
| 5,618,275 A | 4/1997 | Bock | |
| 6,413,216 B1* | 7/2002 | Cain et al. ................. | 600/439 |
| 6,475,148 B1 | 11/2002 | Jackson et al. | |
| 2004/0059219 A1 | 3/2004 | Asafusa | |
| 2004/0082857 A1 | 4/2004 | Schonenberger et al. | |

FOREIGN PATENT DOCUMENTS

| | | |
|---|---|---|
| JP | 6-78930 | 3/1994 |
| JP | 9-502191 | 3/1997 |
| JP | 11-226046 | 8/1999 |
| JP | 2001-507207 | 6/2001 |
| JP | 2001-512329 | 8/2001 |
| JP | 2004-261253 | 9/2004 |
| WO | WO 97/22325 | 6/1997 |
| WO | WO 98/25655 | 6/1998 |
| WO | WO 00/36982 | 6/2000 |

OTHER PUBLICATIONS

Katsuro Tachibana, et al., "The Use of Ultrasound for Drug Delivery", Echocardiography: A Jrnl. of CV Ultrasound & Allied Tech., vol. 18, No. 4, May 2001, pp. 323-328.

(Continued)

*Primary Examiner*—Kevin C Sirmons
*Assistant Examiner*—Bhisma Mehta
(74) *Attorney, Agent, or Firm*—Oblon, Spivak, McClelland, Maier & Neustadt, L.L.P.

(57) ABSTRACT

A method of introducing an ultrasonic drug includes irradiating a low frequency sound wave onto a subject, irradiating a high frequency ultrasonic wave onto a target region of the subject, and introducing the drug into the target region.

2 Claims, 5 Drawing Sheets

OTHER PUBLICATIONS

Jonathan R. Lindner, et al., "Delivery of Drugs with Ultrasound", Echocardiography: A Jrnl. of CV Ultrasound & Allied Tech., vol. 18, No. 4, May 2001, pp. 329-337.

ImaRx Therapeutics Products; 2 pages; http://www.imarx.com/ImaRx/products3_0, Sep. 15, 2006.

Sonitron2000 Sonoporation Gene Transfection System; 16 pages; http://www.nepagene.jp/E/Ecatalogue/Esonitron2.htm, Sep. 15, 2006.

Hiroshi Furuhata, et al., "Development of Ultrasonic Gene Introduction", BME, Japanese Society for Medical and Biological Engineering, vol. 16, No. 7, Jul. 10, 2002, pp. 3-7.

Yoshiaki Tabuchi, et al., "Therapy of Ultrasonic Gene Introduction", separate vol.—medical advance "ultrasonic wave medical science front line", published by Ishiyaku Publishers, Inc., 2004, pp. 203-208.

Katushiko Fujimoto, et al., "Therapy Method and Problem Using Focused Ultrasonic Wave", separate vol.—medical advance "ultrasonic wave medical science front line", published by Ishiyaku Publishers, Inc., 2004, pp. 198-202.

* cited by examiner

METHOD OF INTRODUCING ULTRASONIC DRUG AND APPARATUS THEREOF

CROSS-REFERENCE TO RELATED APPLICATIONS

This application is based upon and claims the benefit of priority from prior Japanese Patent Application No. 2006-001822, filed Jan. 6, 2006, the entire contents of which are incorporated herein by reference.

BACKGROUND OF THE INVENTION

1. Field of the Invention

The present invention relates to a method of introducing an ultrasonic drug and an apparatus thereof, in which an ultrasonic wave is irradiated onto a subject, such as a patient, and introduces agents, such as genes or protein substances, into cells or nucleuses.

2. Description of the Related Art

In recent years, a great deal of attention has recently been given to a therapy method, such as MIT (Minimally Invasive Treatment) or a gene therapy and a regenerative medical technique, which enables a fundamental therapy in early stage. For example, diseases due to arteriascleroses or blood clots, such as an ischemic encephalopathy or a cardiac disease have a high recurrence rate. In Japan, as dietary habits change from Japanese-style food to the west, the number of hyperlipidemia patients has increased. Accordingly, a gene introduction therapy method attracts attention in which a local recurrence is suppressed or a new blood vessel is regenerated in a tissue where infarction occurs, and an ischemia symptom is improved.

A blood vessel regenerating factor accelerates regeneration of a blood vessel with respect to the limb ischemia and necrosis disease of the glycosuria symptom. The bloodstream is reduced due to the ischemia limb disease. In the West, clinical research has been performed on a gene therapy in which a blood vessel factor is introduced into a disrupted diseased part, the bloodstream regeneration is accelerated, and a therapy is performed, and the excellent result has been obtained. A blood vessel regeneration suppressing factor has an opponent function against a blood vessel regeneration factor. A blood vessel regeneration suppressing factor outputs a signal that requires blood vessel regeneration from an active tumor cell of a metabolism, and performs the proliferation. The blood vessel regeneration suppressing factor suppresses regeneration of a nutrient vessel by introducing a blood vessel regeneration factor, and suppresses the proliferation of the tumor.

As a gene therapy, a method is mainly used in which a viral vector is used from the introduction efficiency of the blood vessel regeneration factor. According to the method of using the virus vector, a target gene is introduced into retrovirus or adenovirus whose toxicity is suppressed, and the retrovirus is introduced into a gene of a target cell by the infection. Meanwhile, in recent times, in the West, the person who died due to toxicity of the virus itself has been discovered. As a result, in the inside and outside of the country, cautious theories have been presented with respect to making use of the introduction of the virus gene. In consideration of this phenomenon, another gene introducing method has been examined.

Examples of a non-virus vector method may include a chemical method in which a liposome or the like is used, and an introduction method in which a microinjection, a gene gun, an electroporation, and a laser are used. As an example of the new introduction method, an ultrasonic wave gene introduction technology to which a sonoporation phenomenon by an ultrasonic wave is applied attracts attention.

According to the method of using the ultrasonic wave gene introduction technology, a microjet is generated when an ultrasonic wave contrast medium (bubble) that is used in ultrasonic wave contrast image diagnosis collapses due to the irradiation of the ultrasonic wave, and a phenomenon (sonoporation phenomenon) is used in which a transitory hole is formed in a cell membrane. According to the method that uses the ultrasonic wave gene introduction technology, a gene or a protein is directly introduced into a cell or a nucleus through the hole generated by the sonoporation phenomenon.

Minute bubbles that are referred to as cavitations are generated by the continuous irradiation of the ultrasonic wave. Even this case, the same phenomenon as the sonoporation phenomenon is generated. According to the method that uses the ultrasonic wave gene introduction technology, generally, the bubble (contrast medium) is artificially introduced to improve the introduction efficiency. The methods that use the ultrasonic wave gene introduction technology are disclosed in JP-T-9-502191, JP-T-2001-507207, JP-T-2001-512329, JP-A-2004-261253, JP-A-6-78930, JP-A-11-226046, 'development of ultrasonic gene introduction' by Hiroshi FURUHATA and Yoshinobu MANOBE (BME, Japanese Society for Medical and Biological Engineering, Jul. 10, 2002, vol. 16, No. 7, pp 3 to 7), 'therapy of ultrasonic gene introduction' by Yoshiaki TABUCHI and Takashi KONDO (separate volume•medical advance 'ultrasonic wave medical science front line' published by ishiyaku Publishers, Inc., pp 203 to 208, 2004), and 'therapy method and problem using focused ultrasonic wave' by Katsuhiko FUJIMOTO and Takehide ASANO (separate volume•medical advance 'ultrasonic wave medical science front line' published by ishiyaku Publishers, Inc., pp 198 to 202, 2004).

The ultrasonic wave gene introduction technology is used together with a Levovist in which therapy approval is made as a diagnosis contrast medium or an ultrasonic wave contrast medium such as Optison in which therapy approval is not made as a diagnosis contrast medium, and enhances the drug introducing effect. The Levovist is used when movement of a tissue or the perfusion is observed on an ultrasonic wave diagnosis image. The ultrasonic wave gene introduction technology attracts attention because it enables safe introduction of the drug.

In recent times, in the ultrasonic wave diagnosis, a contrast echo method has been clinically used in which the ultrasonic wave contrast medium (microbubble) is used together. The union of the ultrasonic wave diagnosis and the ultrasonic wave therapy can be easily made. The contrast echo method is very effective as a heating therapy in which a focused ultrasonic wave is used (HIFU: High Intensity Focused Ultrasound) or a monitoring method of an ultrasonic wave therapy in an ultrasonic wave calculus fragmentation device or the like. This technology is disclosed in JP-A-6-78930, JP-A-11-226046, and 'therapy method and problem using focused ultrasonic wave' by Katsuhiko FUJIMOTO and Takehide ASANO (separate volume•medical advance 'ultrasonic wave medical science front line' published by ishiyaku Publishers, Inc., pp 198 to 202, 2004).

As a gene analysis is developed, the introducing of molecular imaging has been rapidly developed in a medical image diagnosis that has remarkably advanced on the basis of the configuration until now. The molecular imaging is largely divided into the two. One is literally one-molecular imaging that images a molecule of a nano order by using light or an X ray. The other is functional imaging that images introduction of the drug in the molecule or the metabolism, and indirectly images the behavior of the molecule. As an example of the former, a fluorescent microscope or an X ray microscope may be exemplified. An example of the latter, a nuclear medicine device (PET, SPECT) or the MRS may be exemplified.

The former is mainly used in a laboratory because of problems of a tissue invasion depth of energy or radiation exposure for imaging. In the case of the latter, nuclear species of a radiation having recognized a target molecular or a contrast medium is combined, the resolution is low but the metabolism function is enhanced, and imaging can be performed. Accordingly, the latter has been clinically used in recent times. In particular, in recent times, a new application like a PET-CT in which the PET and the X-ray CT are combined attracts much attention. In the PET, the resolution is low. In the X-ray CT, a form resolution is high. In the PET-CT, the low resolution of the PET is compensated by the high form resolution of the X-ray CT. The PET-CT displays metabolic information on a three-dimensional form image to overlap.

The molecular image by the molecular imaging images a metabolic-active tumor cell with respect to the normal tissue. In future, a gene that is introduced by a gene introduction technology using a Reporter gene moves normally into the nucleus, an expressed thing is detected by the molecule imaging technology, and the effect of the gene therapy is initially predicted. Accordingly, the molecule image can provide advantageous information together with monitoring of the therapy plan or the ultra-early diagnosis, or gene therapy.

As described above, the drug delivery method attracts attention by the combined use of the ultrasonic wave and the microbubble. However, according to the gene introduction technology using the ultrasonic wave, introduction efficiency is still lower than that in the case of using the birus vector. Since the introduction uses a sonoporation phenomenon by the microjet when the microbubble collapses, the dug can be effectively introduced into the internal organ or the tissue surface that sufficiently comes into contact with the drug. However, the introduction of the drug into the local deep part is very difficult.

BRIEF SUMMARY OF THE INVENTION

Accordingly, it is an object of the present invention to provide a method of introducing an ultrasonic drug and an apparatus thereof, in which when an ultrasonic wave is irradiated onto a living body so as to introduce a gene or a protein, or a drug, the drug can be more effectively introduced into a local part by using a phenomenon that an introduction effect of the drug into a tissue deep part is improved by irradiating the ultrasonic wave in a pressurized state.

According to a first aspect of the invention, a method of introducing an ultrasonic drug includes irradiating a low frequency sound wave onto a subject, irradiating a high frequency ultrasonic wave onto a target region of the subject, and introducing the drug into the target region.

According to a second aspect of the invention, an ultrasonic drug introducing apparatus includes a low frequency pressurizing unit that irradiates a low frequency sound wave onto a subject, a high frequency pressurizing unit that irradiates a high frequency ultrasonic wave onto a target region of the subject, and a timing adjusting unit that adjusts a timing of irradiating the low frequency sound wave onto the subject and a timing of irradiating the high frequency ultrasonic wave onto the subject. In this case, the drug is introduced into the target region by irradiating the low frequency sound wave and the high frequency ultrasonic wave onto the target region.

According to a third aspect of the invention, an ultrasonic drug introducing apparatus includes an ultrasonic wave pressurizing unit that enables a sound wave of at least either a wide band or a plurality of frequencies to be irradiated onto a subject, and a timing adjusting unit that adjusts a timing of irradiating the low frequency sound wave onto the subject and a timing of irradiating the high frequency ultrasonic wave onto the subject. In this case, the drug is introduced into the target region by irradiating the low frequency sound wave and the high frequency ultrasonic wave onto the target region.

DETAILED DESCRIPTION OF THE INVENTION

Hereinafter, a first embodiment of the invention will be described with reference to the accompanying drawings.

Figure 1:
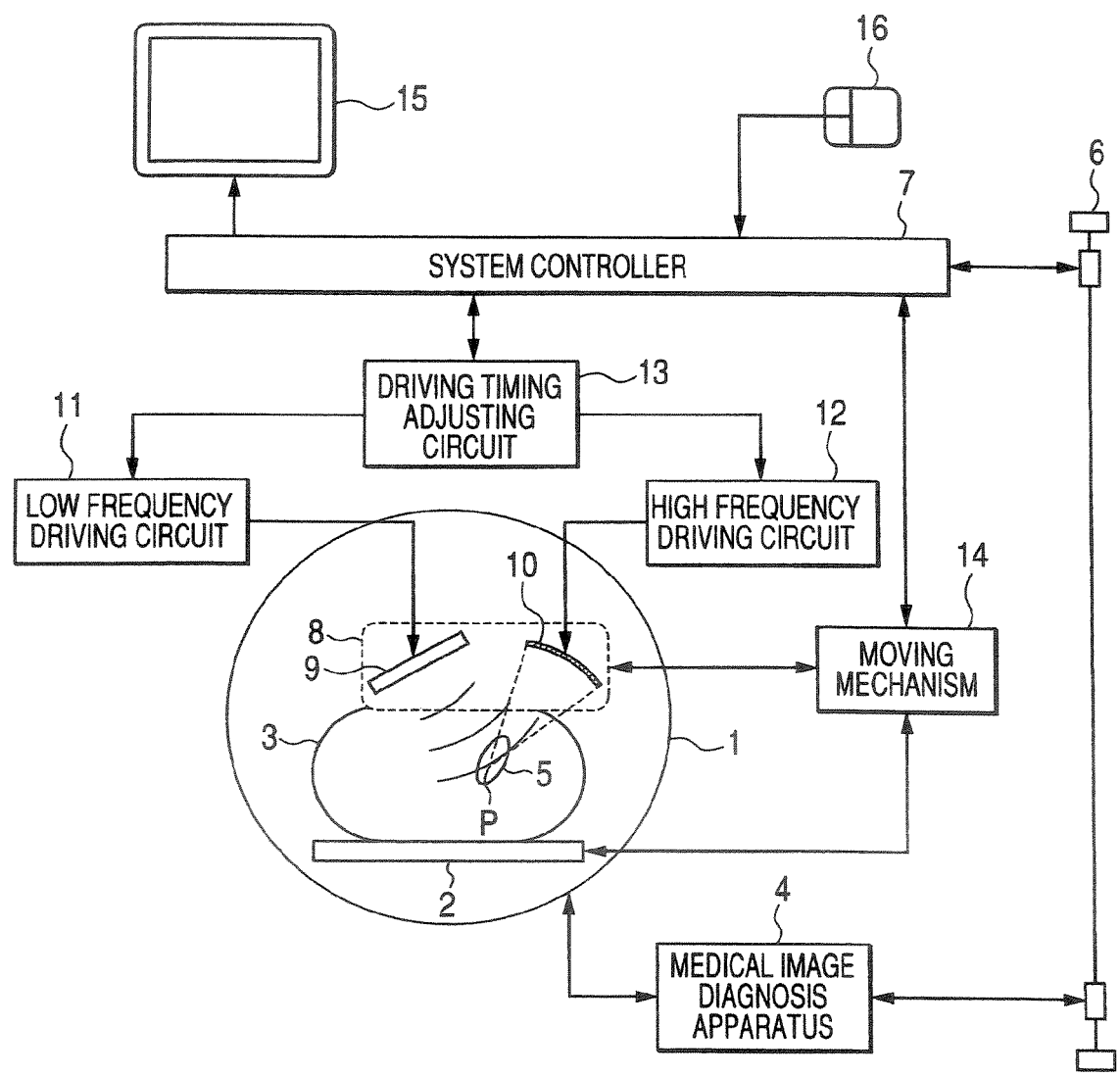
FIG. 1 is a diagram illustrating an entire structure of a medical image diagnosis apparatus that corresponds to an ultrasonic drug introducing apparatus according to a first embodiment of the invention.

FIG. 1 is a diagram illustrating an entire structure of a medical image diagnosis apparatus that includes an ultrasonic drug introducing apparatus. In an imaging apparatus sensor 1 (scanner), a bed 2 is disposed to be freely moved. On the bed 2, a subject 3, such as a patient, is loaded. A medical image diagnosis apparatus 4 is connected to the image device sensor 1. The medical image diagnosis apparatus 4 includes a nuclear medicine device that has an ultrasonic diagnosis device, an MRI device, and a PET device, an X-ray CT device, or a composite device of these devices. The medical image diagnosis apparatus 4 acquires, for example, an ultrasonic image, a MRI image, a PET image, or an X-ray CT image of the subject 3. In addition, the medical image diagnosis apparatus 4 acquires image diagnosis information of the subject 3, and information of a specific portion inside the subject 3, for example, information of a target region 5 into which for example, a gene or a protein, or a drug is introduced. The medical image diagnosis apparatus 4 is connected to a system controller 7 through a network 6. The imaging apparatus sensor 1 performs functional diagnosis, such as shape diagnosis or molecular imaging, together with the medical image diagnosis apparatus 4 while forming a pair each other.

Figure 2:
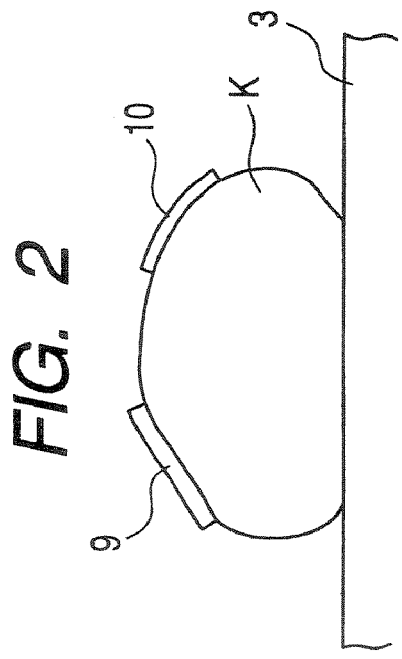
FIG. 2 is a diagram illustrating an inner structure of an applicator in the same apparatus.

In the imaging apparatus sensor 1, an applicator 8 is provided. Further, in the applicator 8, a low frequency oscillator 9 and a high frequency oscillator 10 are provided. As shown in FIG. 2, the low frequency oscillator 9 and the high frequency oscillator 10 are opposite to the subject 3 with a coupling medium K such as a water bag interposed therebetween. The applicator 8 is formed of a material in consideration of the use as the medical image diagnosis apparatus 4, for example, an image diagnosis modality, such as the PET device, the MRI device, or the X-ray CT device. Specifically, if the medical image diagnosis apparatus 4 is the PET device 4, the applicator 8 is formed of a radiation transmitting material. If the medical image diagnosis apparatus 4 is the MRI device, the applicator 8 is formed of a non-magnetic material. If the medical image diagnosis apparatus 4 is the X-ray CT device, the applicator 8 is formed of an X-ray transmitting material. That is, the applicator 8 is formed of a material that does not intercept energy used in image diagnosis and does not affect the medical image.

The low frequency oscillator 9 is connected to a low frequency driving circuit 11. The low frequency oscillator 9 and the low frequency driving circuit 11 form a low frequency pressurizing unit. The low frequency pressurizing unit applies an ultrasonic wave of a low frequency (hereinafter, simply referred to low frequency ultrasonic wave) to the subject 3. The low frequency oscillator 9 irradiates a low frequency ultrasonic wave onto the subject 3 in an unfocused type. The low frequency oscillator 9 is a so-called unfocused type of sound source. The low frequency ultrasonic wave that is emitted from the low frequency oscillator 9 is irradiated over a wide region of the subject 3, for example, irradiated onto the subject 3 to cover the entire subject 3. For example, the low frequency ultrasonic wave that is emitted from the low frequency oscillator 9 has a frequency of approximately several KHz. The low frequency driving circuit 11 supplies the low frequency driving signal to the low frequency oscillator 9 such that the a low frequency ultrasonic wave having a frequency of approximately several KHz is emitted from the low frequency oscillator 9.

The high frequency oscillator 10 is connected to a high frequency driving circuit 12. The high frequency oscillator 10 and the high frequency driving circuit 12 form a high frequency pressurizing unit. The high frequency pressurizing unit applies a high frequency ultrasonic wave to a target region 5 of the subject 3. The high frequency oscillator 10 applies an ultrasonic wave of a high frequency (hereinafter, simply referred to high frequency ultrasonic wave) onto a target region 5 of the subject 3. The high frequency oscillator 10 is a so-called focused type of sound source. The high frequency oscillator 10 is formed in, for example, a spherical piece shape, that is, a spherical shell shape. The high frequency oscillator 10 focuses energy of the corresponding high frequency ultrasonic wave on an introducing focal point P of the high frequency ultrasonic wave. The high frequency oscillator 10 is used as a drug introducing oscillator that accelerates introduction of a gene, a protein, a drug, and the like, into a local part of the subject. For example, the frequency ultrasonic wave that is emitted from the high frequency oscillator 10 has a frequency in a range of several hundred KHz to several MHz. The high frequency driving circuit 12 supplies the high frequency driving signal to the high frequency oscillator 10 such that the a high frequency ultrasonic wave having a frequency in a range of several hundred KHz to several MHz is emitted from the high frequency oscillator 10.

A driving timing adjusting circuit 13 transmits respective timing adjusting signals to the low frequency driving circuit 11 and the high frequency driving circuit 12. The driving timing adjusting circuit 13 transmits the respective timing adjusting signals and adjusts an addition timing of the low frequency ultrasonic wave to the subject 3 and an addition timing of the high frequency ultrasonic wave to the subject 3. Specifically, the driving timing adjusting circuit 13 transmits the respective timing adjusting signal to the low frequency driving circuit 11 and the high frequency driving circuit 12, and adds the high frequency ultrasonic wave to the subject 3 when a pressure by the low frequency ultrasonic wave to be added to the subject 3 becomes a predetermined positive pressure or more, for example, a positive pressure of 1.05 atmospheric pressure or more.

The system controller 7 is connected to the medical image diagnosis apparatus 4 through the network 6. Further, the system controller 7 is connected to a moving mechanism 14, a CRT display 15, and an input device 16 serving as a terminal. For example, the input device 16 has a mouse, and a keyboard.

The system controller 7 receives a PET image, a MRI image, or an X-ray CT image of the subject 3 that is transmitted from the medical image diagnosis apparatus 4 through the network 6, and displays it on the CRT display 15. Further, the system controller 7 receives image diagnosis information of the subject 3 that is transmitted from the medical image diagnosis apparatus 4 through the network 6, or information of a specific part inside the subject 3, for example, information of a target region 5 into which a gene or a protein, or a drug is introduced, and displays it on the CRT display 15.

The system controller 7 receives an operation instruction from the input device 16, and transmits various control signals for performing movement control of the applicator 8 and movement control of the bed 2 to the moving mechanism 14. The moving mechanism 14 performs movement control on a location of the applicator 8 and a location of the bed 2. The system controller 7 receives the operation instruction from the input device 16, irradiates various low frequency and high frequency ultrasonic waves, and transmits an instruction, such as a stop, to the driving timing adjusting circuit 13.

Next, the operation of accelerating the introduction of the drug or the like in the apparatus that has the above-described structure will be described.

The medical image diagnosis apparatus 4 acquires the PET image, the MRI image, or the X-ray CT image as the medical images of the subject 3. Further, the medical image diagnosis apparatus 4 acquires the image diagnosis information of the subject 3, or information of a specific part inside the subject 3, for example, information of a target region 5 into which a gene or a protein, or a drug is introduced. The medical image diagnosis apparatus 4 transmits the medical image of the subject 3, the image diagnosis information of the subject 3, information of the specific part inside the subject 3, for example, information of the target region 5 into which a gene or a protein, or a drug is introduced to the system controller 7 through the network 6.

The system controller 7 receives the medical image, such as, for example, the PET image, the MRI image, the X-ray CT image, or the image diagnosis information of the subject 3, and displays it on the CRT display 15.

An operator operates the input device 16 while observing the CRT display 15, and adjusts the respective locations of the applicator 8 and the bed 2. The system controller 7 receives an operation instruction from the input device 16, and transmits each control instruction to the moving mechanism 14. As a result, the applicator 8 and the bed 2 move, and the location of the subject 3 and an introduction focal point P of the high frequency ultrasonic wave that is emitted from the high frequency oscillator 10 are determined.

On the display screen of the CRT display 15, for example, the PET image, the MRI image, or the X-ray CT image, and a marker indicating the introduction focal point P of the high frequency ultrasonic wave are displayed to overlap each other by the system controller 7. Accordingly, the operator performs an operation instruction for controlling the respective locations of the applicator 8 and the bed 2 such that the marker is located in the target region 5 of the subject 3. Therefore, the applicator 8 comes into contact with the subject 3, and accurate positioning between the introduction focal point P of the high frequency ultrasonic wave and the target region 5 of the subject 3 is performed.

Next, the operator observes the PET image, the MRI image, or the X-ray CT image that is displayed on the display screen of the CRT display 15, and operates the input device 16. Thereby, the system controller 7 operates the low frequency driving circuit 11 and the high frequency driving circuit 12 through the driving timing adjusting circuit 13. As a result, the low frequency oscillator 9 generates the low frequency ultrasonic wave. In this state, if it is determined that a microbubble or a drug sufficiently reaches the target region 5 of the subject 3, the irradiation of the high frequency ultrasonic wave for introduction from the high frequency oscillator 10 is performed.

Figure 3:
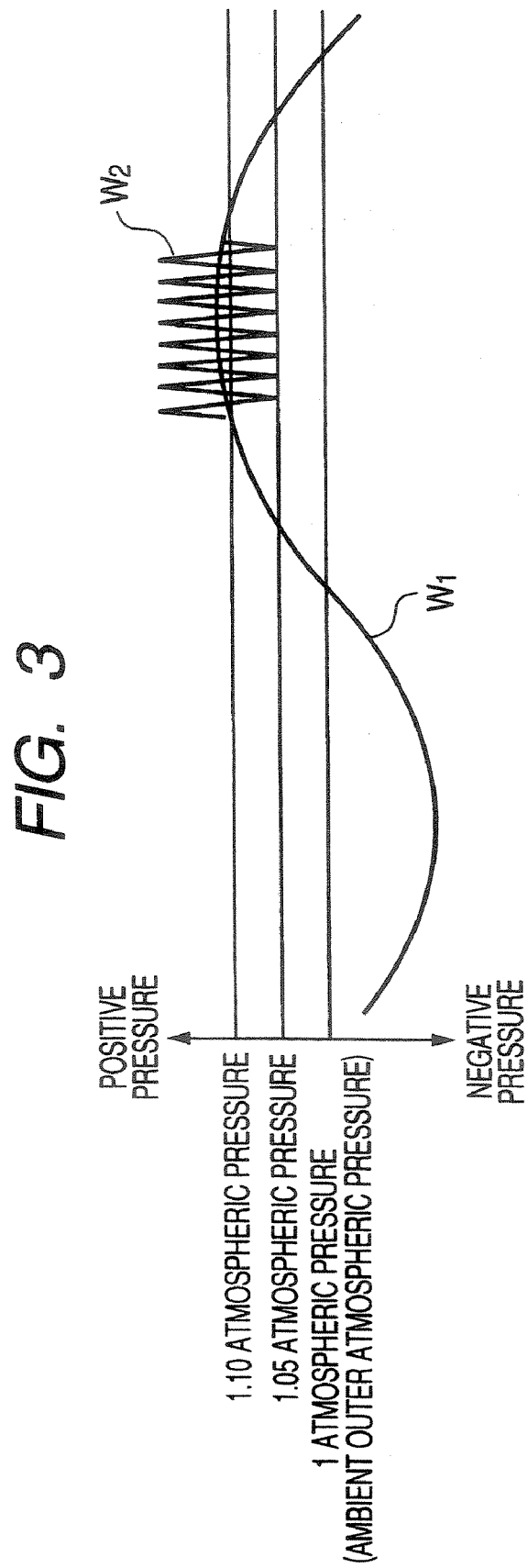
FIG. 3 is a diagram illustrating a time sequence of an overlapping pressure waveform of a low frequency ultrasonic wave and a high frequency ultrasonic wave by the same apparatus.

More specifically, the low frequency oscillator 9 irradiates onto the subject 3, a low frequency ultrasonic wave having a frequency of approximately several KHz in an unfocused type. The low frequency oscillator 9 irradiates the low frequency ultrasonic wave onto the subject 3 such that the low frequency ultrasonic wave covers the entire subject 3. As shown in FIG. 3, the low frequency ultrasonic wave has a waveform $W_1$ of a sine wave of approximately several KHz. The low frequency ultrasonic wave periodically varies in positive and negative atmospheric pressures on the basis of an ambient outer atmospheric pressure (=1 atmospheric pressure) of the subject 3. The low frequency ultrasonic wave, which periodically varies in the positive and negative pressures on the basis of the ambient outer atmospheric pressure (=1 atmospheric pressure), is applied to the local part of the subject into which for example, a gene or a protein, or a drug is introduced.

In a state where the low frequency ultrasonic wave is applied to the target region 5 of the subject 3, during a period of when a positive atmospheric pressure of the low frequency ultrasonic wave reaches, for example, 1.05 atmospheric pressure, the high frequency oscillator 10 irradiates onto the target region 5 of the subject 3, a high frequency ultrasonic wave for drug introduction having a frequency of several hundred KHz to several MHz in a focused type. As shown in FIG. 3, the waveform $W_2$ of the high frequency ultrasonic wave for drug introduction overlaps the low frequency ultrasonic wave during a period of when the low frequency ultrasonic wave is in a positive atmospheric pressure, as shown in FIG. 3. The ultrasonic wave in which the high frequency ultrasonic wave overlaps the low frequency ultrasonic wave is irradiated onto the target region 5 of the subject 3.

As a result, it is possible to accelerate the interaction with microbubble. By means of generation of microjet when the microbubble collapses (sonoporation phenomenon), the introduction of the gene or the protein, or the drug into the target region 5 (diseased part) is accelerated. Further, the driving timing adjusting circuit 13 adjusts a timing such that a pressure wave by the high frequency ultrasonic wave generated from the high frequency oscillator 10 reaches the location of the target region 5 of the subject 3 in a state where a propagation time of an ultrasonic wave in a living body of a patient or the like to be the subject 3 is considered and a pressure waveform by the low frequency ultrasonic wave generated from the low frequency oscillator 9 is in a positive pressure, for example, a positive pressure of 1.05 atmospheric pressure or more, at the location of the target region 5 of the subject 3.

As such, according to the first embodiment, when the pressure by the low frequency ultrasonic wave applied from the low frequency oscillator 9 to the subject 3 becomes a positive pressure of a predetermined positive pressure or more, for example, 1.05 atmospheric pressure or more, the high frequency ultrasonic wave from the high frequency oscillator 10 is applied to the subject 3. When the ultrasonic wave is irradiated onto the living body and the gene or the protein, or the drug is introduced into the living body so as to cure the living body, the high frequency ultrasonic wave for drug introduction is irradiated onto the target region 5 of the subject 3 with a positive pressure application phase. An effect of introducing the drug into a tissue deep part is increased by the ultrasonic wave irradiation in the pressurized state. As a result, effective drug introduction into the local part is improved. Further, it is possible to surely introduce the gene or the protein, or the drug into a local part of the living body of the subject 3, such as the patient. Accordingly, it is possible to achieve a new system that introduces an ultrasonic drug into a local part, which contributes to a gene therapy or a drug delivery therapy.

The applicator 8 is formed of an element that does not affect imaging of each diagnosis modality, such as a nuclear medicine device having an ultrasonic wave diagnosis device, a MRI device, and a PET device, an X-ray CT device, or a composite device of these devices. The introduction of the drug or the like into the target region 5 of the subject 3 can be surely achieved while confirming the target region 5 of the subject 3 by using a molecular image or a detailed shape image.

Further, the first embodiment of the invention may be modified as follows.

The high frequency oscillator 10 may use two or more phased array sound sources, in each of which a plurality of oscillators is disposed in a two-dimensional array. The phased array sound source can perform phase difference driving on the plurality of oscillators. As a result, the phased array sound source can perform focusing of the high frequency ultrasonic wave or electronic scanning of a focal point location. In this case, on the basis of a driving phase of each of the plurality of oscillators, the system controller 7 changes the focusing of the high frequency ultrasonic wave or calculates of a focal point location of the high frequency ultrasonic wave that is electronically scanned. The system controller 7 displays on the CRT display 15, the PET image, the MRI image, or the X-ray CT image, and the calculated focal point location of the high frequency ultrasonic wave is displayed on the displayed image to overlap it.

One oscillator may be constructed to be driven with multiple frequencies without separately providing the low frequency oscillator 9 and the high frequency oscillator 10. In this case, a driving signal, which is obtained by electrically overlapping the respective waveforms of the low frequency driving signal transmitted from the low frequency driving circuit 11 and the high frequency driving signal transmitted from the high frequency driving circuit 12, is supplied to one oscillator.

The low frequency oscillator 9 and the high frequency oscillator 10 may be disposed in the same sound source.

Figure 4A:
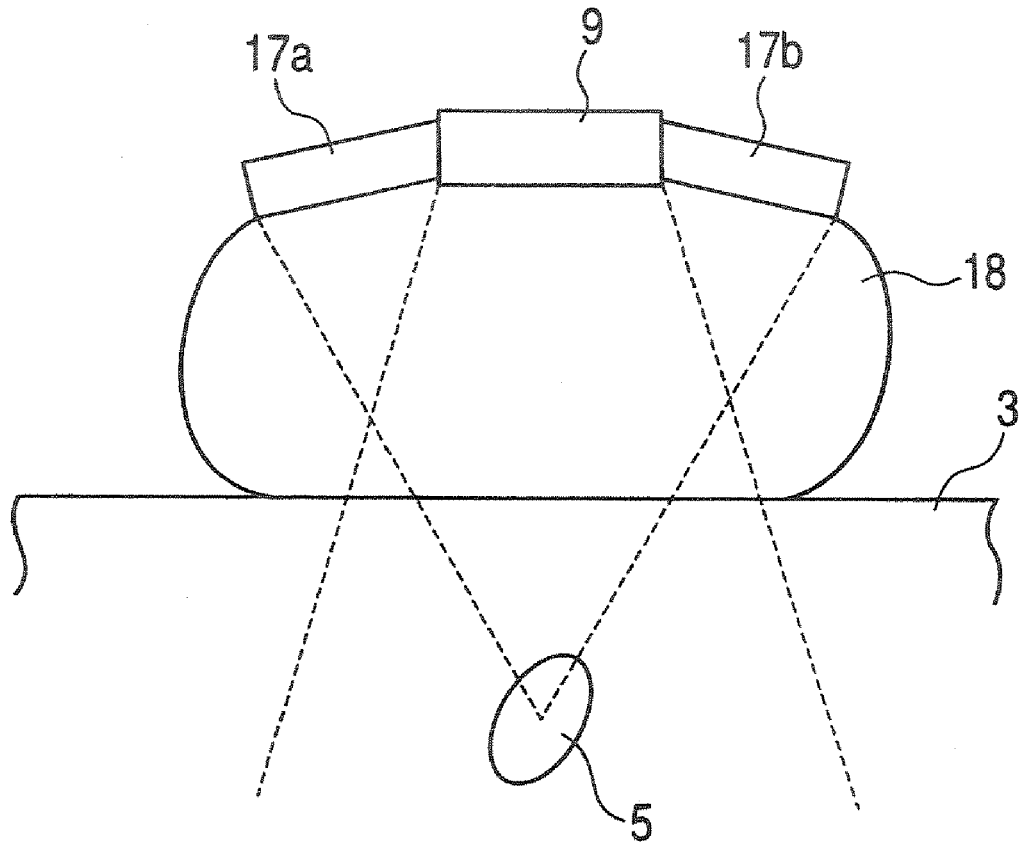
FIG. 4A is a diagram illustrating a structure of a side surface of another sound wave source.
Figure 4B:
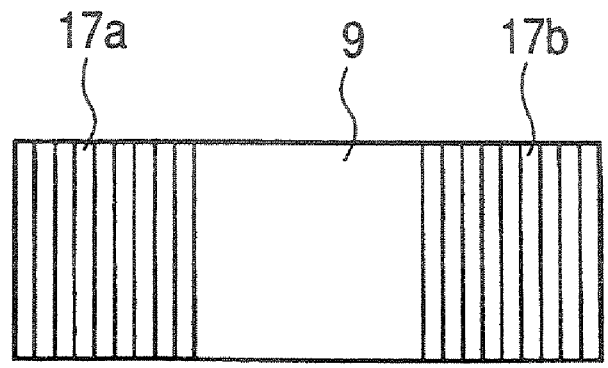
FIG. 4B is a diagram illustrating a structure of a top surface of another sound wave source.

FIGS. 4A and 4B show a structure of another sound wave source. Specifically, FIG. 4A shows a structure of a side surface of another sound wave source, and FIG. 4B shows a structure of a top surface of another sound wave source. The low frequency oscillator 9 applies a low frequency sound wave onto a wide region of the subject 3 in an unfocused type. Phased array sound sources 17a and 17b are respectively disposed on both ends of the low frequency oscillator 9. In each of the phased array sound sources 17a and 17b, a plurality of oscillators are disposed in a two-dimensional array. Each of the phased array sound sources 17a and 17b is provided to be inclined to the low frequency oscillator 9. Each of the phased array sound sources 17a and 17b is inclined in a direction opposite to each other with the low frequency oscillator 9, that is, an inward direction. Each of the phased array sounds 17a and 17b focuses energy of the corresponding high frequency sound wave on an introduction focal point P of the high frequency ultrasonic wave. The high frequency ultrasonic wave that is emitted from each of the phased array sound sources 17a and 17b has a frequency in a range of several hundred KHz to several MHz. The low frequency oscillator 9, and the phased array sound sources 17a and 17b come into contact with the subject 3 through a coupling member 18 having a jellified shape.

In this structure, when the pressure by the low frequency ultrasonic wave applied from the low frequency oscillator 9 to the subject 3 becomes a predetermined positive pressure or more, for example, a positive pressure of 1.05 atmospheric pressure or more, each of the phased array sound sources 17a and 17b applies the high frequency ultrasonic wave to the subject 3.

Figure 5A:
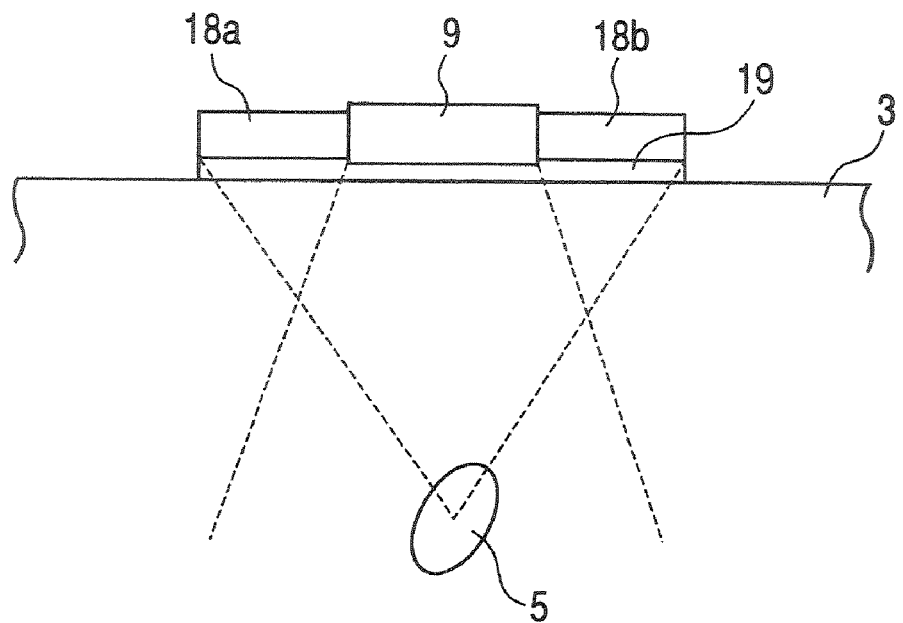
FIG. 5A is a diagram illustrating a structure of a side surface of another sound wave source.
Figure 5B:
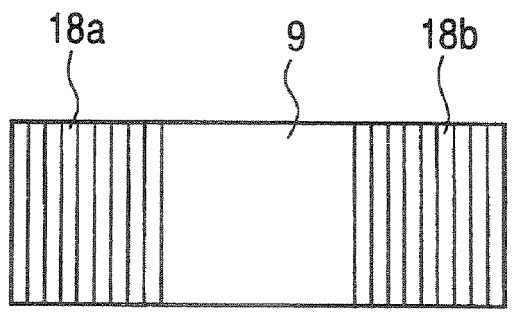
FIG. 5B is a diagram illustrating a structure of a top surface of another sound wave source.
Figure 5C:
FIG. 5C is a diagram illustrating sound lenses that are formed in a phased-array sound source that is the same sound wave source.

FIGS. 5A and 5B show a structure of another sound wave source. Specifically, FIG. 5A shows a structure of a side surface of another sound wave source, and FIG. 5B shows a structure of a top surface of another sound wave source. Phased array sound sources 18a and 18b are respectively disposed on both ends of the low frequency oscillator 9. In each of the phased array sound sources 18a and 18b, a plurality of oscillators are disposed in a two-dimensional array. Each of the phased array sound sources 18a and 18b is provided on the same plane with respect to the low frequency oscillator 9. Each of the phased array sound sources 18a and 18b enables change of a focusing location of a high frequency ultrasonic wave on the basis of a driving phase of each of the plurality of oscillators. The respective phased array sound sources 18a and 18b form a sound lens having a concave shape, as shown in FIG. 5C. As a result, each of the phased array sound sources 18a and 18b focuses energy of the corresponding high frequency ultrasonic wave into the introducing focal point P of the high frequency ultrasonic wave. The high frequency ultrasonic wave that is emitted from each of the phased array sound sources 18a and 18b has a frequency in a range of several hundred KHz to several MHz. The low frequency oscillator 9, and the phased array sound sources 18a and 18b come into contact with the subject 3 through a coupling member 19 having a jellified shape.

In this structure, when the pressure by the low frequency ultrasonic wave applied from the low frequency oscillator 9 to the subject 3 becomes a predetermined positive pressure or more, for example, a positive pressure of 1.05 atmospheric pressure or more, each of the phased array sound sources 18a and 18b applies the high frequency ultrasonic wave to the subject 3.

Next, a second embodiment of the invention will be described with reference to the accompanying drawings. The same components as those of FIG. 1 are denoted by the same reference numeral, and the description thereof will be omitted.

Figure 6:
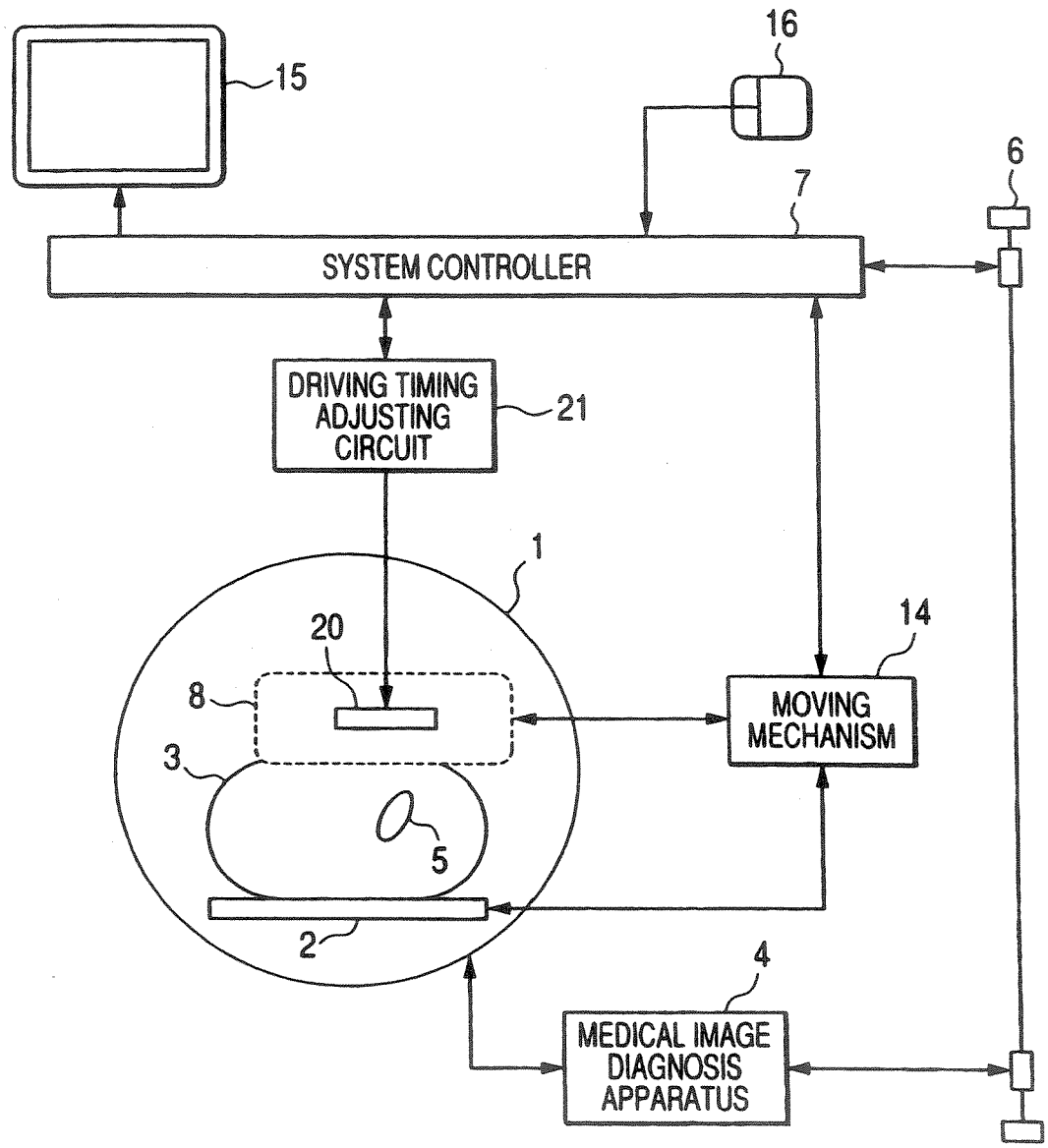
FIG. 6 is a diagram illustrating an entire structure of a medical image diagnosis apparatus that corresponds to an ultrasonic drug introducing apparatus according to a second embodiment of the invention.
Figure 7:
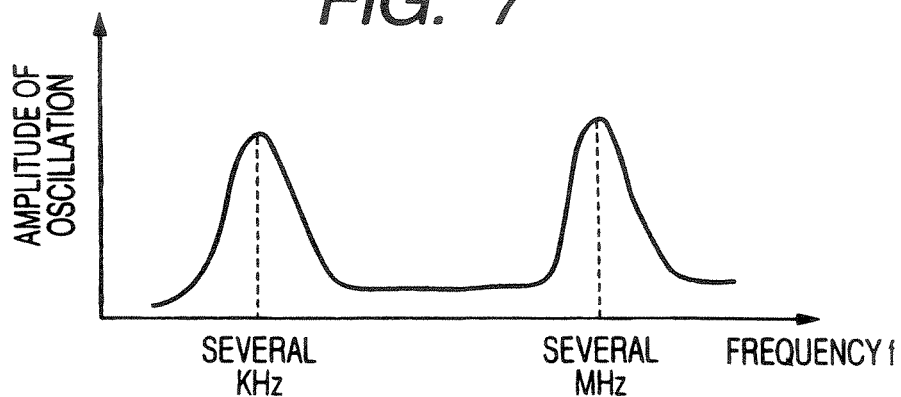
FIG. 7 is a diagram illustrating a frequency characteristic of a composite oscillator in the same apparatus.

FIG. 6 is a diagram illustrating an entire structure of a medical image diagnosis apparatus that includes an ultrasonic drug introducing apparatus. In an application 8, a high frequency and low frequency composite oscillator 20 (hereinafter, simply referred to as composite oscillator) is provided which can oscillate in a wide band or with a plurality of frequencies. For example, as shown in FIG. 7, the composite oscillator 20 oscillates with multiple frequencies of a low frequency ultrasonic wave having a frequency of approximately several KHz and a high frequency ultrasonic wave having a frequency in a range of several hundred KHz to several ten MHz, and overlaps the low frequency ultrasonic wave and the high frequency ultrasonic wave. The composite oscillator 20 irradiates the low frequency ultrasonic wave onto the subject 3 in an unfocused type, and irradiates the high frequency ultrasonic wave onto the target region 5 of the subject 3 in a focused type.

A driving timing adjusting circuit 21 supplies a driving signal, which oscillates from the composite oscillator 20, a low frequency ultrasonic wave having a frequency of approximately several KHz, and oscillates from the composite oscillator 20, a high frequency ultrasonic wave having a frequency in a range of several hundred KHz to several MHz, to the composite oscillator 20. Further, the composite oscillator 20 and the driving timing adjusting circuit 21 form an ultrasonic wave pressurizing unit that enables application of an ultrasonic wave in a wide band or of a plurality of frequencies to the subject 3. Specifically, the driving timing adjusting circuit 21 electrically drives the composite oscillator 20 by a waveform that overlaps the high frequency signal in advance in an enlarged phase of the composite oscillator 20, that is, a compressed wave generating phase. When a pressure by the low frequency ultrasonic wave applied from the composite oscillator 20 to the subject 3 becomes a predetermined positive pressure or more, for example, a positive pressure of 1.05 atmospheric pressure or more, the high frequency ultrasonic wave from the composite oscillator 20 is applied onto the subject 3.

In this case, the composite oscillator 20 irradiates the low frequency ultrasonic wave having a frequency of approximately several KHz onto the subject 3 in an unfocused type, for example, such that the low frequency sound wave covers the entire subject 3. As shown in FIG. 3, the low frequency ultrasonic wave has a waveform $W_1$ of a sine wave of approximately several KHz. The low frequency ultrasonic wave periodically varies in positive and negative atmospheric pressures on the basis of an ambient outer atmospheric pressure (=1 atmospheric pressure) of the subject 3.

In a state where the low frequency ultrasonic wave is applied to the target region 5 of the subject 3, during a period of when a positive atmospheric pressure of the low frequency ultrasonic wave reaches, for example, 1.05 atmospheric pressure, the composite oscillator 20 irradiates onto the target region 5 of the subject 3, a high frequency ultrasonic wave for drug introduction having a frequency of several hundred KHz to several MHz in a focused type. As a result, the waveform $W_2$ of the high frequency ultrasonic wave for drug introduction overlaps the waveform $W_1$ the low frequency ultrasonic wave during a period of when the low frequency sound wave is in a positive atmospheric pressure. The ultrasonic wave in which the high frequency ultrasonic wave overlaps the low frequency ultrasonic wave is irradiated onto the target region 5 of the subject 3.

As a result, it is possible to accelerate the interaction with microbubble. By means of generation of microjet when the microbubble collapses (sonoporation phenomenon), the introduction of the gene or the protein, or the drug into the target region 5 (diseased part) is accelerated.

As described above, according to the second embodiment, the composite oscillator 20 is provided which can oscillate in a wide band or with a plurality of frequencies. When a pressure by the low frequency ultrasonic wave applied from the composite oscillator 20 to the subject 3 becomes a predetermined positive pressure or more, for example, a positive pressure of 1.05 atmospheric pressure or more, the high frequency ultrasonic wave from the composite oscillator 20 is applied onto the subject 3. Therefore, it is possible to achieve the same effect as the first embodiment.

Further, the invention is not limited to the above-described embodiments, and various modifications can be made as follows.

The microbubble that is used when a drug is introduced by using an ultrasonic wave is a material whose detection sensitivity is extraordinarily high in the ultrasonic wave diagnosis device. Accordingly, an ultrasonic wave diagnosis probe is provided in an applicator 8 where the high frequency oscillator 10 or the low frequency oscillator 9 is provided. The density or reaching degree of the microbubble in the target region 5 of the subject 3 can be recognized by detection of the ultrasonic wave diagnosis probe. Accordingly, after recognizing the density or the reaching degree of the microbubble in the target region 5 of the subject 3, the high frequency ultrasonic wave that introduces the gene or the protein, or the drug may be irradiated, and the effect of introducing the corresponding drug or the like may be confirmed by the ultrasonic wave diagnosis device.

That is, by making use of the extraordinary sensitivity with respect to the bubble of the ultrasonic wave, the high frequency ultrasonic wave is irradiated onto the target region 5 of the subject 3 while confirming the target region 5 by using the ultrasonic wave image. Therefore, effective drug introduction can be performed by aiming at a time point when a contrast media is deposited in a wound tissue in the target region 5 of the subject 3. As a result, a therapy effect can be greatly improved, and the amount of used drug can e reduced.

Further, the effect of introducing the drug by using the ultrasonic wave is higher in a continuous wave more than in a pulse wave. It can be confirmed that the effect of introducing the drug is further increased by the variation in the frequency. Accordingly, at the time of being imaged, the bubble distribution is imaged by low MI irradiation that does not collapse the bubble, the low MI irradiation is switched into the high MI continuous irradiation, and an ultrasonic wave for therapy is irradiated. As a result, an effective introduction therapy can be achieved, as compared with a case in which the pulse wave is irradiated as it is.

The ultrasonic wave oscillator for diagnosis in the ultrasonic wave diagnosis device may be used as the high frequency oscillator 10. The ultrasonic wave oscillator for diagnosis supplies the diagnosing high frequency pulse as an introducing pulse. The supply timing of the diagnosing high frequency pulse to the ultrasonic wave oscillator for diagnosis is adjusted, for example, by the driving timing adjusting circuit 21. In this case, the ultrasonic diagnosis device acquires an image of the diseased part of the subject 3 by using a low MI scanner that does not destroy the microbubble. The diagnosis of the diseased part is performed from the image of the diseased part of the subject 3. The introducing high frequency pulse is irradiated onto the diseased part of the subject 3 that is set by the high MI scanner on the basis of the diagnosis result so as to destroy the microbubble, which accelerates the introduction of the gene or the protein, or the drug.

The frequency of the low frequency ultrasonic wave that is emitted from the low frequency oscillator 9 is not limited to approximately several KHz, but may be several ten Hz.

The predetermined positive pressure, for example, the positive pressure of 1.05 atmospheric pressure or more is applied to the subject 3 by irradiating the low frequency ultrasonic wave, but may be applied to the subject 3 by irradiating a sound wave propagating an inner part of the living body or underwater.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic drug introducing apparatus comprising:
   a low frequency pressurizing unit that irradiates a low frequency sound wave which has a frequency of several KHz onto a subject;
   a high frequency pressurizing unit that irradiates a high frequency ultrasonic wave for introduction of a drug and which has a frequency in a range of several hundred KHz to several MHz onto a target region of the subject;
   a timing adjusting unit that adjusts a timing of irradiating the low frequency sound wave onto the subject and a timing of irradiating the high frequency ultrasonic wave onto the subject, and irradiates the high frequency ultrasonic wave for introduction of the drug onto the target region of the subject in a time period when, with the low frequency sound wave irradiated onto the subject, a pressure by the low frequency sound wave reaches a positive pressure of 1.05 atmospheric pressure or more, thereby to promote introduction of the drug into the target region;
   wherein the low frequency pressurizing unit has an unfocused type of low frequency oscillator having ends and that irradiates the low frequency sound wave onto a wide region of the subject,
   the high frequency pressurizing unit has at least two phased array sound sources, a plurality of oscillators being disposed in a two-dimensional array in each phased array sound source, and
   the respective phased array sound sources are disposed on both ends of the low frequency oscillator, respectively.

2. The ultrasonic drug introducing apparatus according to claim 1,
   wherein the high frequency pressurizing unit has a focused type of high frequency oscillator that focuses the high frequency ultrasonic wave and irradiates the high frequency ultrasonic wave onto the subject, and
   the high frequency oscillator has a spherical surface piece shape.

* * * * *